United States Patent [19]

Baldwin et al.

[11] Patent Number: 4,945,182

[45] Date of Patent: Jul. 31, 1990

[54] OCULOSELECTIVE BETA-BLOCKERS

[75] Inventors: John J. Baldwin, Gwynedd Valley; David C. Remy, North Wales; David A. Claremon, Audubon, all of Pa.

[73] Assignee: Merck & Co., Inc., Rahway, N.J.

[21] Appl. No.: 912,871

[22] Filed: Sep. 29, 1986

Related U.S. Application Data

[63] Continuation-in-part of Ser. No. 813,324, Dec. 24, 1985, abandoned.

[51] Int. Cl.$^5$ ............................................. C07C 93/06
[52] U.S. Cl. ..................................... 564/349; 514/913
[58] Field of Search .................. 564/345; 514/652, 913

[56] References Cited

U.S. PATENT DOCUMENTS

| | | | |
|---|---|---|---|
| 3,466,376 | 9/1969 | Brandstrom et al. | 564/349 X |
| 3,541,130 | 11/1970 | Koppe et al. | 564/349 X |
| 3,542,872 | 11/1970 | Koppe et al. | 564/349 X |
| 3,555,161 | 1/1971 | Brandstrom et al. | 564/349 X |
| 3,644,469 | 2/1972 | Koppe et al. | 564/349 X |
| 3,663,607 | 10/1985 | Barrett et al. | |
| 3,872,147 | 3/1975 | Koppe et al. | 564/349 X |
| 3,888,898 | 6/1975 | Koppe et al. | 564/349 X |
| 3,892,799 | 7/1975 | Pinhas. | |
| 3,930,016 | 12/1975 | Berntsson et al. | |
| 4,066,768 | 1/1978 | Raabe et al. | |
| 4,085,136 | 4/1978 | Tucker | 564/349 X |
| 4,146,638 | 3/1979 | Renth et al. | 564/349 X |
| 4,171,370 | 10/1985 | Jonas et al. | |
| 4,402,976 | 9/1983 | Muir | 514/913 X |
| 4,450,172 | 5/1984 | Yoo. | |
| 4,515,814 | 10/1985 | Wick et al. | |
| 4,522,829 | 6/1988 | Harting et al. | 514/913 X |

FOREIGN PATENT DOCUMENTS

| | | |
|---|---|---|
| 833291 | 9/1975 | Belgium. |
| 0041295 | 5/1981 | European Pat. Off. . |
| 0082461 | 12/1982 | European Pat. Off. . |
| 1966513 | 5/1973 | Fed. Rep. of Germany. |
| 1260848 | 1/1972 | United Kingdom. |

*Primary Examiner*—Robert V. Hines
*Attorney, Agent, or Firm*—William H. Nicholson; Joseph F. DiPrima

[57] ABSTRACT

Hydroxyalkyl-phenoxy-propan-2-ol-3-amines are oculoselective $\beta$-blockers useful in the treatment of elevated intraocular pressure with little or no effect on the pulmonary or cardiovascular system.

3 Claims, No Drawings

OCULOSELECTIVE BETA-BLOCKERS

SUMMARY OF THE INVENTION

This is a continuation-in-part of copending application, Ser. No. 813,324 filed Dec. 24, 1985 now abandoned.

This invention is concerned with a compound of structural formula I:

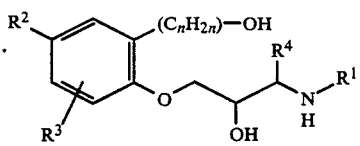

or an ophthalmologically acceptable salt thereof, wherein $R^1$, $R^2$, $R^3$, $R^4$, and n are as hereinafter defined.

It is also concerned with a method of treating elevated intraocular pressure and the disease states associated therewith, such as glaucoma, by topical ocular administration of a compound of structural formula I.

The invention is also concerned with ophthalmic formulations of a compound of structural formula I, and processes for preparing such compounds.

BACKGROUND OF THE INVENTION

Glaucoma is an ocular disorder associated with elevated ocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that a few β-adrenergic blocking agents are effective in reducing intraocular pressure. While many of these agents are effective in reducing intraocular pressure, they also have other characteristics, e.g. local anesthetic activity, that are not acceptable for chronic ocular use.

(S)-1-tert-butylamino-3-[(4-morpholino-1,2,5-thiadiazol-3-yl)oxy]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

However, known β-adrenergic blocking agents have not been shown to demonstrate any meaningful oculoselectivity and, in spite of the low dose normally required for ocular administration, manifest their β-blocking properties in extra-ocular tissue, especially the pulmonary and cardiovascular systems to such an extent that they should not be administered to patients with pulmonary or cardiovascular ailments.

Now, with the present invention there are provided compounds, with pronounced oculoselective β-blocking properties with little or no liability by way of extraocular β-blocking activity; ophthalmic formulations of those compounds; methods of treating elevated intraocular pressure with those compounds and their ophthalmic formulations and processes for preparation of those compounds.

DETAILED DESCRIPTION OF THE INVENTION

One embodiment of this invention is the novel compound of structural formula I:

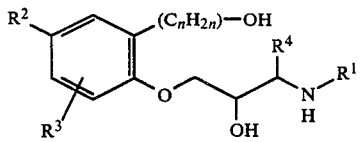

or an ophthalmologically acceptable salt thereof, wherein $R^1$ is $C_{1-5}$alkyl, either straight or branched chain, especially isopropyl or tertiary butyl;

$R^2$ is $C_{1-3}$alkyl, either straight or branched chain, especially methyl;

$R^3$ is
(1) hydrogen,
(2) $C_{1-3}$alkyl, either straight or branched chain,
(3) $C_{1-3}$alkoxy, either straight or branched chain,
(4) halo, such as fluoro, chloro, bromo or iodo, especially fluoro or chloro, or
(5) cyano;

$R^4$ is hydrogen or $C_{1-3}$alkyl; and n is 1–5, to form a straight or branched chain alkylene; especially $-(CH_2)_2-$.

For treatment of elevated intraocular pressure it is preferred that $R^1$ is t-butyl or isopropyl and $R^3$ is hydrogen. It is further preferred that n is 2.

The ophthalmologically acceptable salts of the compounds of this invention include those prepared from inorganic acids such as hydrochloric, and those formed from organic acids such as maleic acid, citric acid, pamoic acid, pyruvic acid, fumaric acid, oxalic acid, tartaric acid or the like.

All of the novel compounds of this invention are propan-2-ol-3-amines in which the 2-carbon carrying the hydroxyl group is asymmetric giving rise to (R)- and (S)-enantiomers with respect to that asymmetric center.

Either enantiomer or mixtures of the (S)- and (R)-enantiomers such as the racemic mixtures are useful in treating elevated intraocular pressure and each form a part of this invention.

If $R^4$ is other than hydrogen, i.e., $C_{1-3}$ alkyl, a second asymmetric carbon is introduced and it too has (S)- and (R)-enantiomeric forms, and the hydroxyl group and the $R^4$ group can be threo or erythro oriented.

Also, substituents $R^1$, $R^2$, $R^3$, and $-(C_nH_{2n})-$ may themselves be capable of isomerism. This invention includes all of the possible isomers and all of the possible mixtures comprising two or more of those isomers contributed by $R^1$, $R^2$, $R^3$ and $(C_nH_{2n})-$.

A second embodiment of this invention are novel processes for preparing the above described novel compounds. One process is depicted by the following reaction scheme:

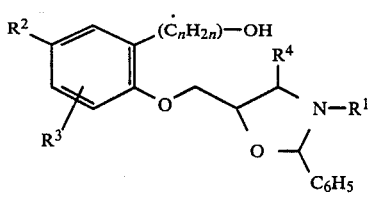

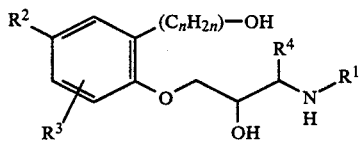

The oxazolidine ring is opened by treating it with a dilute mineral acid, especially about 0.1N HCl optionally in the presence of a buffering agent such as sodium acetate, or the like, at about 5° C. to 30° C., preferably room temperature for about 3 to 10 hours.

After isolating the free base, it may be converted to an acid addition salt, if desired, by dissolving it in an inert organic solvent such as ether, adding a solution of the acid in an inert organic solvent, and collecting the precipitated salt.

Another process particularly useful for preparing the compounds wherein $R^4$ is lower alkyl is depicted as follows:

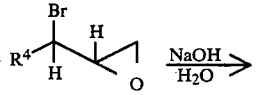
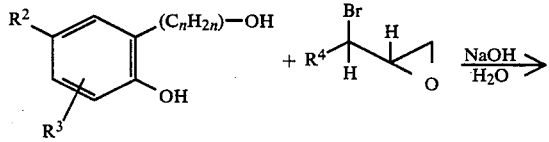

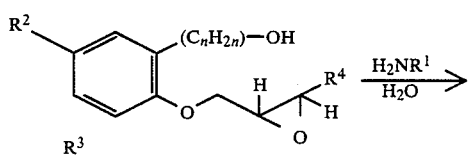

The phenol and the 1-bromoalkyl-oxirane are stirred together in an ethereal solvent such as 1,2-dimethoxyethane, diglyme, THF or the like for 48 to 96 hours, preferably about 72 hours. The resulting phenoxymethyloxirane is then treated with an amine of formula $R^1NH_2$ in water at about 80° to 100° C., preferably reflux temperature for about 3 to 7 hours.

Another process is particularly useful for preparing the compounds wherein $R^4$ is lower alkyl and the (S)(S)-diastereomer is desired. The process is depicted as follows:

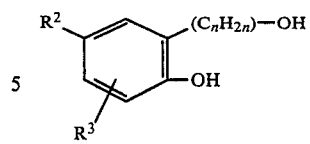

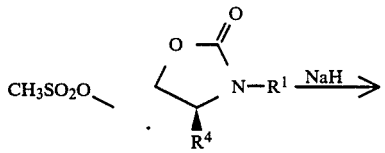

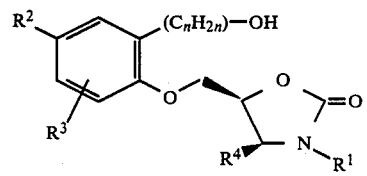

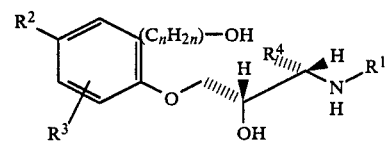

The first step is conducted by warming the phenol and sodium hydride in DMSO at about 50°–70° C. followed by addition of the mesyloxymethyloxazolidin-2-one and aging at 50°–70° for about 2–5 hours.

The isolated phenoxymethyloxazolidin-2-one is then heated at about 80°–100° C. for about 18 to 36 hours in lower alkanolic aqueous caustic such as sodium or potassium hydroxide.

A third embodiment of this invention is the method of treating elevated intraocular pressure by the topical ocular administration to a patient in need of such treatment of an effective intraocular pressure lowering amount of a compound of formula I or an ophthalmologically acceptable salt thereof.

A unit dose comprises about 0.001 to 5.0 mg, preferably about 0.005 to 2.0 mg, and especially about 0.05 to 1.0 mg of active compound per eye. Multiple unit doses are administered as needed to achieve and maintain a normotensive or close to normotensive ocular condition.

Some of the compounds of structure I are generically disclosed in U.S. Pat. No. 3,872,147 and British Patent No. 1,260,848. Any hydroxyalkylphenyl-β-blockers that are specifically known, are known primarily as intermediates in the synthesis of the corresponding ethers. They are also known to have weak β-blocking properties on cardiovascular and pulmonary β-receptors. However, with this invention it has been discovered in the ortho oriented hydroxyalkylphenyl-β-blockers that surprisingly if $R^2$ is para to the traditional β-blocker side chain and is lower alkyl, especially methyl, the compounds are outstandingly selective in producing an ocular effect, i.e. reducing elevated intraocular pressure while having only minimal effect on extraocular tissue.

On the other hand, if $R^2$ is hydrogen, the compounds are essentially inactive or much less active at reasonable dose levels in reducing intraocular pressure.

The relative activities discussed above are clearly depicted in Table I. Compounds 2, 4 and 6 have —CH$_3$ groups ($R^2$) in the para position and show excellent lowering of intraocular pressures in the α-chymotrypsinized rabbit model after topical application of 0.1% and 0.5% solutions of the drug.

Compounds 1 and 3, on the other hand, without the para-alkyl group are essentially ineffective and Compound 5 is only slightly effective in lowering intraocular pressure in α-chymotrypsinized rabbits.

α-Chymotrypsinized Rabbit Model Test Procedure:

Rabbits are anesthetized with intravenous ketamine (18–25 mg/kg). The right eye is proptosed and alpha-chymotrypsin (50 UAE, Pharmacopee francaise) dissolved in 200 μl of sterile saline (0.9% NaCl) is injected through the pupil into the posterior chamber using an S-curved 30 gauge-needle. During the injection, the tip of the needle is swept across the posterior chamber to distribute the enzyme. After removing the needle, the eyes are treated with 1 or 2 drops of an antibiotic (Triantibiotique ®, M.S.D.-Chibret, or chloramphenicol, M.S.D.-Chibret). Rabbits subsequently showing severe eye inflammation are discarded. The IOP of the operated animals are checked after approximately four weeks and animals with an elevated pressure of 30 mmHg or more are used at least one month after injection of the enzyme. Group mean IOP of injected rabbits is greater than 40 mmHG, i.e. approximately 20 or more mmHg above the value observed in normal, untreated rabbit eyes.

The results are expressed as mean ± standard deviation in mmHg and are the change in IOP from the testing level measured just prior ($t_o$) to administration of test substance or vehicle. The significance of the data is determined as the difference from the $t_o$ value using Dunnett's "t" test.

The results are as described in Table I.

TABLE I

| | $R^1$ | $R^2$ | $R^4$ | Stereo-chem | α-CMT[1] mmHg/conc. |
|---|---|---|---|---|---|
| 1 | $CH_3$<br>\|<br>—C—$CH_3$<br>\|<br>$CH_3$ | H | H | (S)— | 0.6/0.5% |
| 2 | $CH_3$<br>\|<br>—C—$CH_3$<br>\|<br>$CH_3$ | $CH_3$— | H | (S)— | 8.6/0.5%<br>7.50/0.1% |
| 3 | $CH_3$<br>\|<br>—CHCH$_3$ | H | —$CH_3$ | erythro- | 1.2/0.5% |
| 4 | $CH_3$<br>\|<br>—CHCH$_3$ | $CH_3$ | —$CH_3$ | erythro- | 8.0/0.5%<br>5.3/0.1% |
| 5 | $CH_3$<br>\|<br>—CHCH$_3$ | H | —$CH_3$ | threo- | 4.7/0.5% |
| 6 | $CH_3$<br>\|<br>—CHCH$_3$ | $CH_3$ | —$CH_3$ | threo- | 8.2/0.5% |

(1) lowering of intraocular pressure in mm of Hg in α-chymotrypsinized rabbit/concentration of test substance (w/v)

A fourth embodiment of this invention is the novel ophthalmic formulations comprising one of the novel compounds as active ingredient. The ophthalmic composition of this invention may be in the form of a solution, suspension, ointment, gel or solid insert and contains about 0.01 to 5% and especially about 0.5 to 2% by weight of medicament. Higher concentrations as, for example about 10% or lower concentrations can be employed.

The pharmaceutical preparation which contains the compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600; carbowaxes 1,000, 1,500, 4,000, 6,000 and 10,000; antibacterial components such as quaternary ammonium compounds, phenylmercuric salts known to have cold sterilizing properties and which are non-injurious in use, thimerosal, methyl and propyl paraben, benzyl alcohol, phenyl ethanol; buffering ingredients such as sodium chloride, sodium borate, sodium acetates, gluconate buffers; and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a solid insert. For example, one may use a solid water soluble polymer as the carrier for the medicament. The polymer used to form the insert may be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates such as polyacrylic acid salts, ethylacrylates, polyacrylamides; natural products such as gelatin, alginates, pectins, tragacanth, karaya, chondrus, agar, acacia; the starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, and mixtures of said polymers.

EXAMPLE 1

(S)-2-(3-((1,1-dimethylethyl)amino)-2-hydroxypropoxy)-5-methyl-benzeneethanol maleate Step A:

Preparation of 2-(2-hydroxy-5-methylphenyl)ethanol

A solution of 8.34 g (0.05 mol) of 2-allyl-4-methylphenol in 420 ml of CH$_3$OH containing a few crystals of Sudan III indicator was cooled to −78° C. Ozone was passed through this solution until a color change of the Sudan III indicator showed that the ozonization reaction was complete. Solid sodium borohydride (6.4 g) was added in small portions to the cold solution. When this addition was complete, the solution was allowed to warm to room temperature overnight. The solution was made acid by the addition of 6N HCl, and then was concentrated to dryness in vacuo. The residue was dissolved in ethyl acetate and was washed with water, saturated NaHCO$_3$ solution and brine. The solution was dried, filtered, and evaporated to give 7.3 g (96%) of 2-(2-hydroxy-5-methylphenyl)ethanol.

Step B:

Preparation of
(S)-2-[5-methyl-2-(2-phenyl-3-(2-(1,1-dimethylethyl)oxazolidin-5-yl-methoxy)phenyl]ethanol To a stirred solution of 7.3 g (0.048 mol) of 2-(2-hydroxy-5-methylphenyl)ethanol in 30 ml of dry DMF was added 1.91 g (0.048 mol) of sodium hydride (60% in mineral oil). The mixture was stirred at room temperature until hydrogen evolution ceased, and the solution was heated at 60° C. for 30 minutes to insure complete reaction. The solution was cooled to room temperature, and to this solution was added 18.29 g of 3-(1,1-dimethylethyl)-2-phenyl-5-(toluenesulfonyloxymethyl)oxazolidine prepared by the reaction of 11.29 g (0.048 mol) of (S)-3-tert-butyl-5-hydroxymethyl-2-phenyloxazolidine with 9.15 g (0.048 mol) of p-tosylchloride. The solution was heated at 120° C. overnight. The cooled solution was poured onto 600 ml of water and this mixture was extracted with four 150 ml portions of ethyl acetate. The combined ethyl acetate extracts were washed with water, dilute sodium hydroxide solution, water, and brine. The solution was dried over sodium sulfate, filtered, and concentrated in vacuo to afford 16.1 g of crude product.

Step C:

Preparation of
(S)-2-(3-((1,1-dimethylethyl)amino)-2-hydroxypropoxy)-5-methylbenzeneethanol maleate A mixture of 2.5 g (0.0068 mol) of product from Step B and 30 ml of 1N HCl was heated on a steam bath for 15 minutes. The cooled solution was extracted with ether (3×100 ml). The aqueous phase was made basic with a solution of sodium bicarbonate and this mixture was extracted with chloroform (3×100 ml). The combined chloroform extracts were dried (Na$_2$SO$_4$), filtered, and the solvent evaporated to give 1.1 g of crude product as the free base. This material was purified by flash chromatography on silica gel using 5% methanol in chloroform saturated with ammonia gas to develop the column. Evaporation of the solvent afforded 0.79 g of chromatographically homogeneous free base product. A maleate salt was prepared and was recrystallized from ethyl acetate; m.p 71°–73° C.; [α]$_{589}$= −18.0° (C, 0.723; CH$_3$OH).

Anal. Calcd. for C$_{16}$H$_{27}$NO$_3$·C$_4$H$_4$O$_4$: C, 60.43; H, 7.86; N, 3.53. Found: C, 60.16; H, 8.01; N, 3.48.

The corresponding (R)-enantiomer was prepared similarly and had m.p. 72°–75° C., [α]$_{589}$= +17.6° (C, 0.723; CH$_3$OH).

Employing the procedures substantially as described in Example 1, but using the reactants depicted in the following reaction scheme, there are produced the compounds described in Table II:

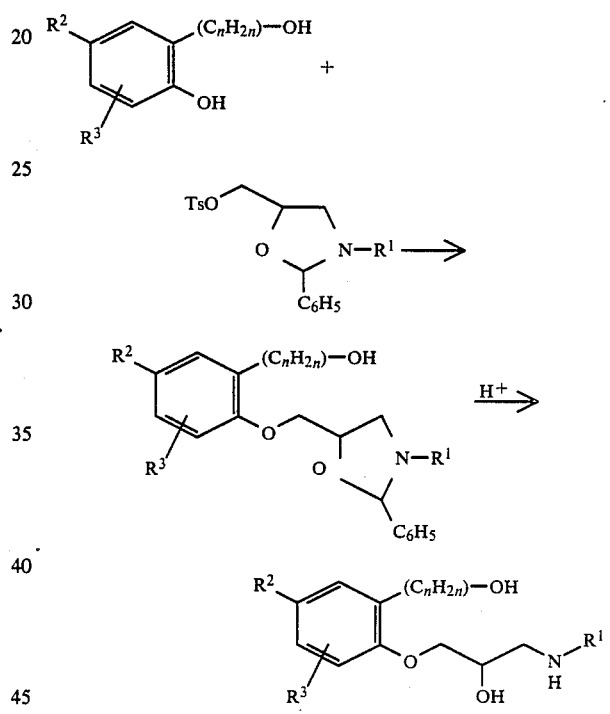

TABLE II

| Stereo-Chemistry | R$^1$ | R$^2$ | R$^3$ | (C$_n$H$_{2n}$)OH |
|---|---|---|---|---|
| (S)— | —CH(CH$_3$)$_2$ | —CH$_3$ | H | —(CH$_2$)$_2$OH |
| (S)— | —C(CH$_3$)$_3$ | —C$_2$H$_5$ | F | —(CH$_2$)$_2$OH |
| (S)— | —CH(CH$_3$)$_2$ | —CH$_3$ | —CH$_3$ | —(CH$_2$)$_2$OH |
| (S)— | —CH(CH$_3$)$_2$ | —CH$_3$ | H | —(CH$_2$)$_3$OH |
| (S)— | —C(CH$_3$)$_3$ | —CH$_3$ | H | —(CH$_2$)$_3$OH |
| (S)— | —C(CH$_3$)$_3$ | —CH$_3$ | H | OH<br>|<br>—CH$_2$CH—CH$_3$ |
| (S)— | —C(CH$_3$)$_3$ | —CH$_3$ | H | CH$_3$<br>|<br>—CH$_2$—C—OH<br>|<br>CH$_3$ |
| (S)— | —CH(CH$_3$)$_2$ | —CH(CH$_3$)$_2$ | H | —(CH$_2$)$_2$OH |
| (S)— | —CH(CH$_3$)$_2$ | —CH$_3$ | —OCH$_3$ | —(CH$_2$)$_2$OH |

EXAMPLE 2

Erythro-2-(2-hydroxy-3-((1-methylethyl)amino)butoxy)-5-methyl-benzeneethanol ethanedioate salt A mixture of 5.04 g (0.033 mole) of 2-(2-hydroxyethyl)-3-methylphenol, 1.33 g (0.033 mole) of sodium hydroxide in 135 ml of water, and 5.00 g (0.033 mmole) of erythro-(1-bromoethyl)oxirane in 25 ml of 1,2-dimethoxyethane was stirred at room temperature for about 72 hours. The mixture was extracted with 5×100 ml of ether. The extract was washed with dilute sodium hydroxide solution, dilute brine and saturated brine, dried over MgSO$_4$ and concentrated in vacuo to give 4.25 g (58%) of 2-methyl-3-[2-(2-hydroxyethyl)phenoxymethyl]oxirane. A 1:1 (v/v) mixture of 1-methylethylamine and water (130 ml) was added to the oxirane and the mixture was heated at reflux for 5 hours, and concentrated in vacuo to dryness. The residue was dissolved in ether, dried over MgSO$_4$ and concentrated to dryness to give 2.90 g of oil. The oil was flash chromatographed on a silica gel column by elution with 3% CH$_3$OH in CHCl$_3$ saturated with ammonia gas to give 0.5 g of product. Conversion to the oxalate salt gave material with m.p. 138°–140° C. (0.5 isopropanol solvate).

Using threo-(1-bromoethyl)oxirane in the above process there was produced threo-2-(2-hydroxy-3-((1-methylethyl)amino)butoxy)-5-methyl-benzeneethanol which was isolated as the hydrochloride salt, hemihydrate as an amorphous foam.

Calculated for C$_{16}$H$_{27}$NO$_3$.HCl.0.5H$_2$O; C, 58.79; H, 8.94; N, 4.29% Found C, 58.94; H, 9.73; N, 4.39%.

Employing the procedure substantially as described in Example 2, but using the starting materials and reagents indicated in the following reaction scheme, there are produced the products and intermediates described in Table III.

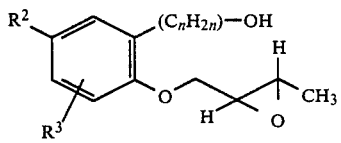

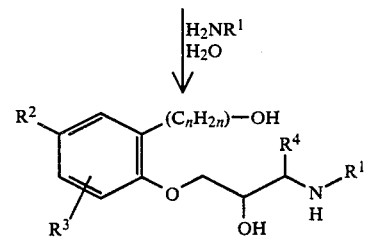

TABLE III

| R$^1$ | R$^2$ | R$^3$ | R$^4$ | (C$_n$H$_{2n}$)OH |
|---|---|---|---|---|
| —CH(CH$_3$)$_2$ | —CH$_3$ | H | —CH$_2$CH$_3$ | —(CH$_2$)$_2$OH |
| —C(CH$_3$)$_3$ | —C$_2$H$_5$ | F | —CH$_3$ | —(CH$_2$)$_2$OH |
| —CH(CH$_3$)$_2$ | —CH$_3$ | —CH$_3$ | —CH$_3$ | —(CH$_2$)$_2$OH |
| —CH(CH$_3$)$_2$ | —CH$_3$ | H | —CH$_3$ | —(CH$_2$)$_3$OH |
| —C(CH$_3$)$_3$ | —CH$_3$ | H | —CH$_3$ | OH<br>  \|<br>—CH$_2$CH—CH$_3$ |
| —C(CH$_3$)$_3$ | —CH$_3$ | H | —CH$_3$ | CH$_3$<br>  \|<br>—CH$_2$—C—OH<br>  \|<br>CH$_3$ |
| —CH(CH$_3$)$_2$ | —CH(CH$_3$)$_2$ | H | —CH$_3$ | —(CH$_2$)$_2$OH |
| —CH(CH$_3$)$_2$ | —CH$_3$ | —OCH$_3$ | —CH$_3$ | —(CH$_2$)$_2$OH |

EXAMPLE 3

(S)(S)-2-(2-hydroxy-3-((1-methylethyl)amino)butoxy)-5-methyl-benzeneethanol ethanedioate

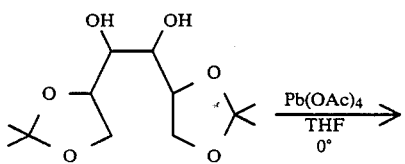

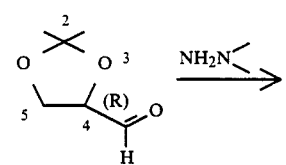

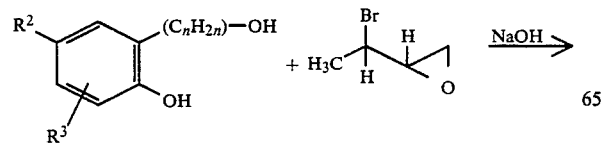

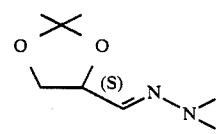

Step A:

Preparation of (S)-2,2-Dimethyl-4-formyl-1,3-dioxolan-N,N-dimethyl hydrazone Mannitol diacetonide (60 g) in 300 ml of THF (anhydrous) at 0° C. under Argon was stirred and treated with 102.0 g of Pb(OAc)$_4$ over 15 minutes. After an additional 15 minutes at 0° C. the reaction was warmed to 22° C. and stirred 45 minutes, then recooled to 0° C., and filtered through a filter aid. Cold THF (150 ml) was used to wash the lead salts and the filtrate was stirred at 0° C. under Argon and treated with 1,1-dimethylhydrazine (120 ml, anhydrous) in one portion. After 45 minutes at 0° C., 75 grams of anhydrous MgSO$_4$ was added and stirring was continued at room temperature for 2 hours. The inorganics were removed by vacuum filtration and the reaction mixture was concentrated at reduced pressure to an oily solid which was dissolved in 500 ml of CH$_2$Cl$_2$ and washed with H$_2$O, aqueous Na$_2$CO$_3$, and brine. The organic portion was separated, dried (Na$_2$SO$_4$) and concentrated to an oil which was homogenous by TLC; yield 67 grams (85%).

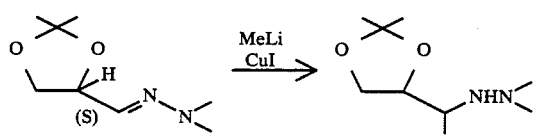

Step B:

Preparation of (S)(RS)-2,2-dimethyl-4-[1-(N$^2$,N$^2$-dimethylhydrazino)ethyl-1,3-dioxolan The product from Step A (25.0 g, 145.3 mmol) in 100 ml of anhydrous diethylether was added dropwise to a cold (−35° C.) solution of 155 ml of CH$_3$Li (1.4M in ether) and 2.77 grams of CuI under Argon. The reaction was warmed to −10° C. over 3 hours and allowed to react at 0° C. over 3 hours. Methanol (6 ml) followed by saturated aqueous NH$_4$Cl solution (100 ml) was added and the organic layers separated. The aqueous phase was extracted with CH$_2$Cl$_2$ (3×250 ml), the combined organic layers were washed with brine, dried (Na$_2$SO$_4$) and concentrated to an oil. The oil was dissolved in ether and reconcentrated twice then dissolved in ether and filtered through filter aid. Concentration afforded 24.9 grams (91%) of product as a mixture (3:1) of diastereomers as yellow oil.

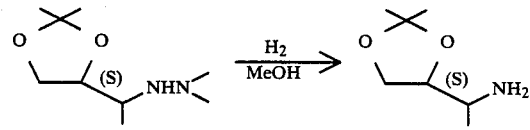

Step C:

Preparation of (S)(RS)-2,2-dimethyl-4-(1-aminoethyl)-1,3-dioxolan

The product from Step B (50 grams) was reduced using 500 grams of Raney nickel at 50 PSI in 1000 ml of methanol for 24 hours to give after filtration and concentration 47 grams of amine as an oil.

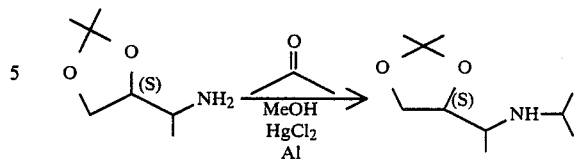

Step D:

Preparation of (S)(RS)-2,2-dimethyl-4-[1-(N-methylethyl)ethyl]-1,3-dioxolan

To 50.2 grams of amine from Step C in 700 ml of methanol under Argon was added 260 ml of acetone and cooled to 0° C. Aluminum metal as strips of foil was added (49 grams) followed by 1.3 grams of HgCl$_2$. This was stirred at 22° C. for 24 hours and then filtered through filter aid and concentrated to a yellow oil to yield 55 grams of product.

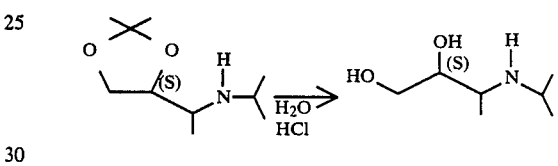

Step E:

(S)(RS)-1,2-dihydroxy-3-[(1-methylethyl)amino]butane

The amine from Step D (55 g) in 350 ml of H$_2$O was treated while cooling in an ice bath with 50 ml of concentrated HCl. After 4 hours at 0° C. the reaction mixture was extracted with CH$_2$Cl$_2$ (3×150 ml). The aqueous phase was neutralized with 50% aqueous NaOH and concentrated at reduced pressure to 150 ml. The aqueous phase was extracted with 5×300 ml of n-butanol. The organic portions were dried (Na$_2$SO$_4$) and concentrated to an oil to yield 41.62 grams (82%) of product.

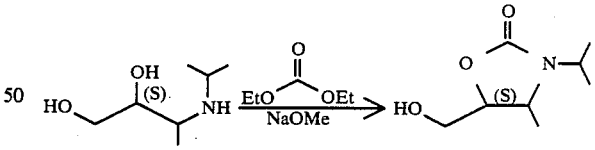

Step F:

Preparation of (S)(RS)-5-hydroxymethyl-4-methyl-3-(1-methylethyl)oxazolidin-2-one To 14.2 g of crude glycolamine from Step E in 67 ml of diethylcarbonate at 60° C. was added 7.09 g of NaOCH$_3$ over 10 minutes under Argon. The mixture was heated to 130° C. and the ethanol was removed by distillation. After 1.5 hours the mixture was cooled to 22° C., diluted with H$_2$O and extracted with CH$_2$Cl$_2$ (3×100 ml). The organic portions were washed with brine, dried (Na$_2$SO$_4$) and concentrated to an oil to yield 14.0 grams of crude product.

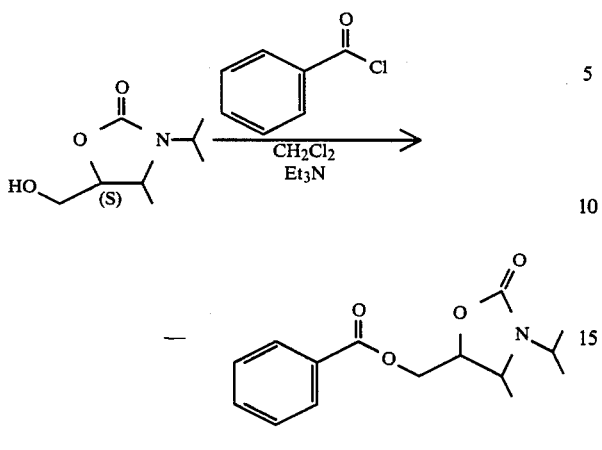

Step G:

(S)(RS)-5-benzoyloxymethyl-4-methyl-3-(1-methylethyl)oxazolidine-2-one

Crude oxazolidinone (14.0 g, 81 mmol) was dissolved in 200 ml of $CH_2Cl_2$ and 16.9 ml of triethylamine. Benzoyl chloride (10.3 ml, 89 mmol) was added at 0° C. and the mixture was allowed to reach 22° C. and stirred 2 hours. This was washed with $H_2O$, saturated $Na_2CO_3$ solution and brine, dried ($MgSO_4$) and chromatographed on silica gel (20% ethyl acetate in hexane) to give the two pure benzoate diastereomers. The less chromatographically polar isomer was assigned the stereochemistry shown:

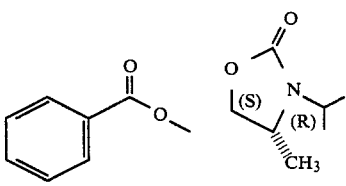

m.p. = 57–58° C.
$[\alpha]_D = +53.7°$ C.
(C = 2.0 mg/ml, MeOH)

and the more polar isomer was assigned the following stereochemistry:

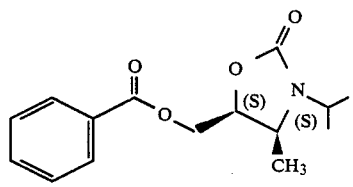

m.p. = 61–62° C.
$[\alpha]_D = +69.96$
(C = 2.43 mg/ml, MeOH)

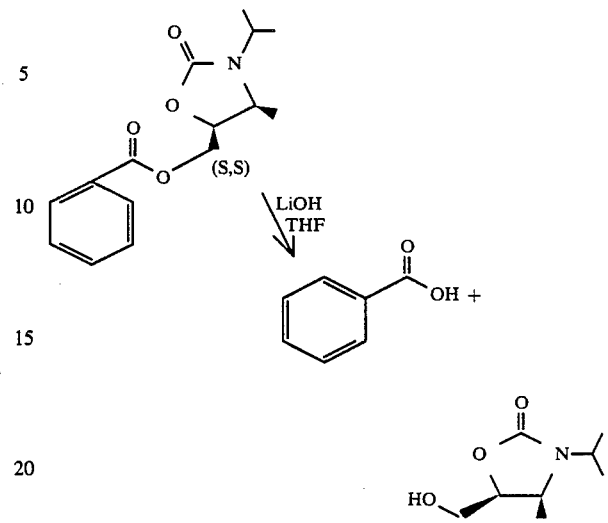

Step H:

Preparation of (S)(S)-5-hydroxymethyl-4-methyl-3-(1-methylethyl)oxazolidin-2-one A THF (87 ml) solution of 4.80 grams of (S)(S)-oxazolidinone from Step G was stirred at 22° C. and treated with 87 ml of 1N LiOH in $H_2O$. After 2.5 hours at 22° C. the THF was removed by rotary evaporation and the product extracted with $CH_2Cl_2$. The combined organic portions were washed with saturated aqueous $Na_2CO_3$, $H_2O$, and brine, dried ($Na_2SO_4$) and concentrated to essentially pure product as a white foam; yield 2.93 g (95%).

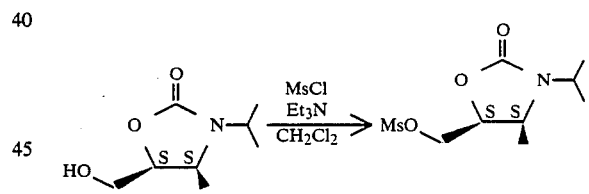

Similarly prepared is the 5(S)-hydroxymethyl-4(R)-methyl-3-(1-methylethyl)oxazolidin-2-one.

Step I:

Preparation of (S)(S)-5-methanesulfonyloxymethyl-4-methyl-3-(1-methylethyl)oxazolidin-2-one Crude hydroxy oxazolidinone (2.93 g, 16.9 mmol) was dissolved in 17.0 ml of anhydrous $CH_2Cl_2$ and cooled to $-20°$ C. An hydrous triethylamine (3.53 ml, 1.5 equivalents) was added dropwise followed by 1.94 grams (1.31 ml, 16.9 mmol) of methanesulfonyl chloride. This was allowed to reach $-10°$ C. over 2 hours then treated with $H_2O$. The organic layer was separated. The aqueous phase was extracted with $CH_2Cl_2$ and the combined organics were extracted with 1.0N HCl, 5% aqueous $NaHCO_3$, and brine, dried ($Na_2SO_4$) and concentrated to an oily foam; yield 4.50 grams (100%).

Similarly prepared is the 5(S)-methanesulfonyloxymethyl-4(R)-methyl-3-(1-methylethyl) oxazolidin-2-one.

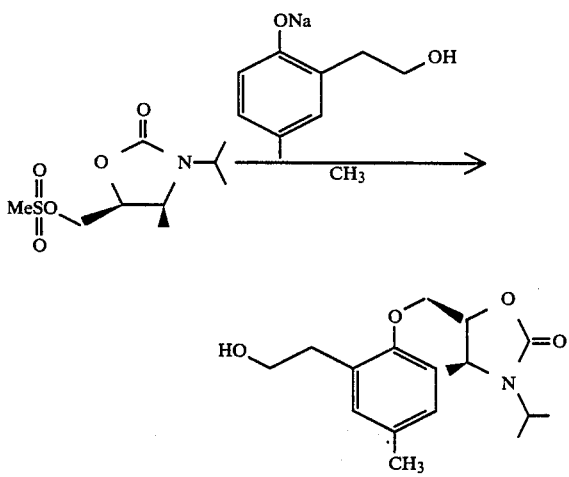

Step J:

Preparation of (S)(S)-5-(2-hydroxyethyl-4-methylphenoxymethyl)-4-methyl-3-(1-methylethyl)oxazolidin-2-one To 1.00 g of 60% NaH (in oil) suspended in 25 ml of anhydrous DMSO was added 4.05 g (26.6 mmol) of 2-(2-hydroxyethyl)-4-methylphenol as a solid. This mixture was warmed to 60° C. and maintained at 60° C. until H$_2$ evolution ceased. Mesylate (4.50 g, 16.9 mmol) from Step I, dissolved in 37 ml of DMSO was added via syringe and the mixture was maintained at 60° C. for 3 hours and at 25° C. for 12 hours under Argon. The reaction mixture was diluted with H$_2$O and extracted with CH$_2$Cl$_2$ (3×125 ml). The organic portion was washed with 5% aqueous NaOH (4×70 ml) and brine, dried (MgSO$_4$), concentrated and flash chromatographed (silica gel; 30% 100% ethyl acetate in hexane) to give 3.53 g (71%) of pale yellow oil product.

Similarly prepared is the 5(S)-(2-hydroxyethyl-4-methylphenoxymethyl)-4(R)-methyl-3-(1-methylethyl)oxazolidin-2-one.

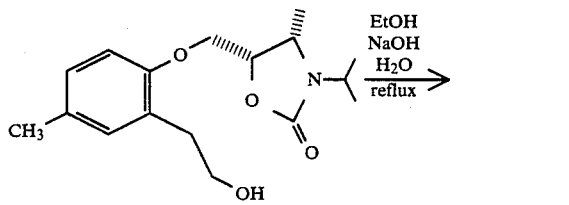

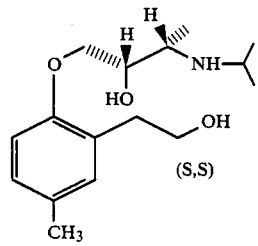

Step K:

Preparation of (S)(S)-2-(2-hydroxy-3-((1-methylethyl)amino)butoxy)-5-methylbenzeneethanol ethanedioate The oxazolidinone from Step J was dissolved in degassed ethanol (80 ml) and aqueous 10% NaOH (80 ml). The mixture was refluxed under Argon for 24 hours. After cooling and acidifying with concentrated HCl (18 ml) the mixture was extracted with ethyl acetate. The aqueous portion was made basic (pH 10) with solid Na$_2$CO$_3$ and extracted with CH The organic portion was dried (Na$_2$SO$_4$) and concentrated to an oil to give 2.50 g of product as the free base (80%). The free base was converted to its oxalate salt by dissolving it in isopropyl alcohol and adding 0.80 g of oxalic acid. This was concentrated and triturated with ethyl acetate and hexane to give 2.23 g of the oxalate salt as a solvate containing 1/5 mole of hexane; m.p. 109°–114° C.

Similarly prepared is the 2-(2(S)-hydroxy-3(R)-((1-methylethyl)amino)butoxy)-5-methylbenzeneethanol ethanedioate.

Examples of topical ocular formulations follows:

EXAMPLE 4

| Solution Composition | |
|---|---|
| (S)-2-(3-(1,1-dimethylethyl)amino)-2-hydroxypropoxy)-5-methyl-benzene-ethanol maleate | 6.8 mg. |
| Sodium Chloride | 7.4 mg. |
| Benzalkonium chloride | 0.10 mg. |
| Sodium acetate anhydrous | 0.82 mg. |
| Water for injection q.s. ad. | 1.0 ml. |

The active compound, salts, and benzalkonium chloride are added to and dissolved in water and the final solution diluted to volume. The solution is rendered sterile by filtration through a sterilizing filter.

EXAMPLE 5

| | |
|---|---|
| (S)-2-(3-((1,1-dimethylethyl)amino)-2-hydroxypropoxy)-5-methyl-benzene-ethanol maleate | 5 mg. |
| Petrolatum q.s. ad. | 1 gram |

The active compound and the petrolatum are aseptically combined.

EXAMPLE 6

| | |
|---|---|
| (S)-2-(3-((1,1-dimethylethylamino)-2-hydroxypropoxy)-5-methyl-benzene-ethanol maleate | 1 mg. |
| Hydroxypropylcellulose q.s. | 12 mg. |

Ophthalmic inserts are manufactured from compression molded films which are prepared on a Carver Press by subjecting the powder mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrated insert are then autoclaved at 250° F. for ½ hour.

EXAMPLE 7

| | |
|---|---|
| (S)-2-(3-((1,1-dimethylethylamino)-2-hydroxypropoxy)-5-methyl-benzene-ethanol maleate | 1 mg. |
| Hydroxypropyl cellulose q.s. ad. | 12 mg. |

Ophthalmic inserts are manufactured from a solvent cast film prepared by making a viscous solution of the powder using methanol as the solvent. The solution is placed on a Teflon plate and allowed to dry at ambient conditions. After drying, the film is placed in an 88% R.H. cabinet until it is pliable. Appropriately sized inserts are cut from the film.

EXAMPLE 8

| | |
|---|---|
| (S)-2-(3-((1,1-dimethylethylamino)-2-hydroxypropoxy)-5-methyl-benzene-ethanol maleate | 1 mg. |
| Hydroxypropyl methyl cellulose q.s. ad. | 12 mg. |

Ophthalmic inserts are manufactured from a solvent case film which is prepared by making a viscous solution of the powder blend using a methanol/water solvent system (10 ml. methanol is added to 2.5 g. of powder blend, to which 11 ml. of water (in three divided portions) is added. The solution is placed on a Teflon plate and allowed to dry at ambient conditions. After drying, the film is placed in an 88% R. H. cabinet until it is pliable. Appropriately sized inserts are then cut from the film.

EXAMPLE 9

| | |
|---|---|
| (S)-2-(3-((1,1-dimethylethylamino)-2-hydroxypropoxy)-5-methyl-benzene-ethanol maleate | 1 mg. |
| Hydroxypropymethyl cellulose | 12 mg. |
| q.s. ad. | |

Ophthalmic inserts are manufactured from compression molded films which are prepared on a Carver Press by subjecting the powder mixture of the above ingredients to a compressional force of 12,000 lbs. (gauge) at 350° F. for one minute. The film is cooled under pressure by having cold water circulate in the platen. Ophthalmic inserts are then individually cut from the film with a punch. Each insert is placed into a vial, which is then placed in a humidity cabinet (88% R.H. at 30° C.) for two to four days. After removal from the humidity cabinet, the vials are stoppered and then capped. The vials containing the hydrated insert are then autoclaved at 250° F. for one-half hour.

What is claimed is:

1. A compound of structural formula:

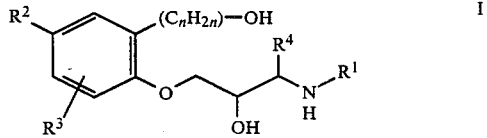

which includes the (R) and (S)-enantiomer, mixtures of the (S) and (R) enantiomers and the threo and erythro-diastereomers and the individual enantiomer thereof or an ophthalmologically acceptable salt thereof, wherein:

$R^1$ is t-butyl or isopropyl;
$R^2$ is $C_{1-3}$alkyl;
$R^3$ is hydrogen;
$R^4$ is hydrogen or $C_{1-3}$alkyl; and
n is 1–5.

2. The compound of claim 1 or an ophthalmologically acceptable salt thereof wherein n is 2.

3. The compound of claim 2, which is:
(R) or (S)-2-(3-((1,1-dimethylethyl)amino)-2-hydroxypropoxy)-5-methyl-benzeneethanol;
threo or erythro-2-(2-hydroxy-3-((1-methylethyl)amino)butoxy)-5-methylbenzeneethanol; or
an ophthalmologically acceptable salt thereof.

* * * * *